US008497402B2

(12) United States Patent
Iwasaki et al.

(10) Patent No.: US 8,497,402 B2
(45) Date of Patent: Jul. 30, 2013

(54) PROCESS AND APPARATUS FOR PRODUCING GAS HYDRATE PELLET

(75) Inventors: Toru Iwasaki, Ichihara (JP); Masahiro Takahashi, Ichihara (JP); Takashi Arai, Ichihara (JP); Shinji Takahashi, Tokyo (JP); Kouhei Takamoto, Tamano (JP); Kenji Ogawa, Tokyo (JP); Masafumi Aoba, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 0 days.

(21) Appl. No.: 13/557,469

(22) Filed: Jul. 25, 2012

(65) Prior Publication Data

US 2012/0285083 A1 Nov. 15, 2012

Related U.S. Application Data

(62) Division of application No. 12/733,899, filed as application No. PCT/JP2007/069396 on Oct. 3, 2007, now Pat. No. 8,303,293.

(51) Int. Cl.
*C07C 9/00* (2006.01)
*B28B 5/10* (2006.01)

(52) U.S. Cl.
USPC .......... 585/15

(58) Field of Classification Search
None
See application file for complete search history.

(56) References Cited

U.S. PATENT DOCUMENTS

| | | | |
|---|---|---|---|
| 2,675,304 | A | 4/1954 | Komarek |
| 4,017,241 | A | 4/1977 | Papinchak et al. |
| 2001/0001670 | A1 | 5/2001 | Krismanth et al. |
| 2005/0035479 | A1 | 2/2005 | Guzmann et al. |
| 2006/0112617 | A1 | 6/2006 | Clark et al. |

FOREIGN PATENT DOCUMENTS

| | | | |
|---|---|---|---|
| AU | 2002306357 | B2 | 3/2006 |
| JP | 2002-220353 | A | 8/2002 |
| JP | 2003-287199 | A | 10/2003 |
| JP | 2006-104256 | A | 4/2006 |
| JP | 2007-254531 | A | 10/2007 |
| JP | 2007-269908 | A | 10/2007 |
| JP | 2007-270029 | A | 10/2007 |
| WO | 03/006589 | A1 | 1/2003 |

*Primary Examiner* — Mary F Theisen
(74) *Attorney, Agent, or Firm* — Jacobson Holman PLLC

(57) ABSTRACT

Provided is a process and an apparatus for producing at low cost gas hydrate pellets having an excellent storability. A gas hydrate generated from a raw-material gas and raw-material water is dewatered and simultaneously molded into pellets with compression-molding means under conditions suitable for generating the gas hydrate while the gas hydrate is generated from the raw-material gas and the raw-material water that exist among particles of the gas hydrate.

6 Claims, 21 Drawing Sheets

(b)

(a)

PROCESS AND APPARATUS FOR PRODUCING GAS HYDRATE PELLET

CROSS-REFERENCE TO RELATED APPLICATIONS

This application is a divisional of U.S. application Ser. No. 12/733,899, filed Mar. 26, 2010, which is a national stage of PCT/JP07/069396 filed Oct. 3, 2007 and published in Japanese, both of which are hereby incorporated by reference.

BACKGROUND OF THE INVENTION

1. Field of the Invention

The present invention relates to a process and an apparatus for producing gas hydrate pellets by compression-molding a gas hydrate, and more specifically relates to a process and an apparatus for producing gas hydrate pellets, which are capable of producing at low cost gas hydrate pellets having an excellent storability.

2. Description of Related Art

In these days, as safe and economical means for transporting and storing a natural gas or the like (hereinafter, called a "raw-material gas"), a method using a gas hydrate obtained by hydrating the raw-material gas into a solid hydrate has been in the limelight. A gas hydrate is generally generated by reacting a raw-material gas and water under low temperature, high pressure conditions. The gas hydrate thus generated is in the form of a slurry containing 40 to 60% by weight of water. For this reason, a technique for storing the gas hydrate has been employed in which the gas hydrate content is increased to approximately 90% by weight by dewatering, regeneration, or the like, and then the gas hydrate is compression-molded at atmospheric pressure into a product (hereinafter, called "pellets") in an almond form, a lens form, a spherical form, or an indeterminate form (for example, refer to Patent Document 1). This technique has a problem in that a large part of the gas hydrate pellets, which are stored at a temperature of −20° C. and atmospheric pressure, is decomposed in a short time period.

For solving such a problem, Patent Document 2 proposes the following method. Specifically, a gas hydrate having such a particle size that the decomposition thereof is suppressed by the self-preservation effect is separated to be stored through classification. The gas hydrate that is removed through the classification is decomposed and the gas hydrate is regenerated from the result of the decomposition.

However, such a method requires facilities for the classification and the rehydration of gases, thus leading to an increase in the production cost for gas hydrate pellets.

Patent Document 1: Japanese patent application Kokai publication No. 2002-220353

Patent Document 2: Japanese patent application Kokai publication No. 2003-287199

BRIEF SUMMARY OF THE INVENTION

An object of the present invention is to provide a process and an apparatus for producing gas hydrate pellets, which are capable of producing at low cost gas hydrate pellets having an excellent storability.

A process for producing gas hydrate pellets, according to the invention, to achieve the above object is characterized in that a gas hydrate generated from a raw-material gas and raw-material water is dewatered and simultaneously molded into pellets with compression-molding means under conditions suitable for generating the gas hydrate while the gas hydrate is generated from the raw-material gas and the raw-material water that exist among particles of the gas hydrate.

In addition, a process for producing gas hydrate pellets according to the invention is characterized in that a gas hydrate having a gas hydrate concentration of 40 to 70% by weight is dewatered and simultaneously compression-molded into pellets with compression-molding means under conditions suitable for generating the gas hydrate.

It is preferable to use, for the compression-molding means, briquetting rolls including a pair of rolls each having a plurality of pellet molds in an outer peripheral surface thereof, the pair of rolls rotating respectively in opposite directions to each other.

In addition, it is preferable that the gas hydrate is made from a natural gas, and that the generating conditions are a pressure of 1 to 10 MPa and a temperature of 0 to 10° C.

An apparatus for producing gas hydrate pellets, according to the invention, to achieve the above object is an apparatus for producing gas hydrate pellets that produces gas hydrate pellets by compression-molding a gas hydrate, the apparatus for producing gas hydrate pellets, characterized by including: a pair of compression rolls each having a plurality of molds in an outer peripheral surface thereof, the pair of compression rolls rotating respectively in opposite directions to each other; and feeding means for feeding the gas hydrate between the pair of compression rolls.

It is preferable that dewatering means for the gas hydrate is provided between the pair of compression rolls and the feeding means.

It is preferable that a pair of dewatering rolls rotating respectively in opposite directions to each other are used for the dewatering means, and that at least one of the pair of dewatering rolls has a plurality of drain grooves formed in an outer peripheral surface thereof and arranged in a circumferential direction and/or an axial direction of the dewatering roll.

In addition, it is preferable that drain means for discharging water generated by the compression-molding of the gas hydrate is provided.

It is preferable that the drain means is formed of: a water-shield plate covering at least an upper half of end faces of the pair of compression rolls; and a drain pipe penetrating the water-shield plate. It is preferable that the drain means is formed of: a drain pipe penetrating a wall face of the hopper included in the feeding means; or any one of a slit and a labyrinth that is formed in a wall face of the hopper. The drain means may be formed of a drain gutter disposed close to the pair of compression rolls.

It is preferable that the drain means is formed of a drain hole communicatively connecting between each mold and an end face of a corresponding one of the pair of compression rolls, that an inner diameter of the drain hole is 0.5 to 5 mm, and that a water-permeable material is disposed on a surface of each mold.

Moreover, the drain means may be formed of: a water-absorbent material attached on a flat surface portion of the outer peripheral surface; and a dewatering roller pressing the water-absorbent material.

An apparatus for producing gas hydrate pellets according to the invention is characterized by including: a first roll that rotates; a second roll and a third roll which are arranged close to and in parallel with the first roll, and each of which rotates in an opposite direction to that in which the first roll rotates; and feeding means for feeding a gas hydrate between the first roll and the third roll, characterized in that the second roll has a plurality of molds formed in an outer peripheral surface thereof, and the gas hydrate is dewatered by the first roll and the third roll, and subsequently the dewatered gas hydrate is compression-molded by the first roll and the second roll.

It is preferable that at least one of the first and third rolls has a plurality of drain grooves formed in an outer peripheral surface thereof and arranged in a circumferential direction and/or an axial direction thereof.

Through the process according to the invention for producing gas hydrate pellets, in which a gas hydrate generated from a raw-material gas and raw-material water is dewatered and simultaneously molded into pellets with compression-molding means under conditions suitable for generating the gas hydrate while the gas hydrate is generated from the raw-material gas and the raw-material water that exist among particles of the gas hydrate, and wherein a gas hydrate having a gas hydrate concentration of 40 to 70% by weight is dewatered and simultaneously compression-molded into pellets with compression-molding means under conditions suitable for generating the gas hydrate, a void ratio can be reduced to substantially 0% by forming a gas remaining in a void among particles, water on surfaces of the particles, and wedge water into a hydrate, thereby compressing the void. Accordingly, high-density gas hydrate pellets having a high gas content can be produced. Further, the gas hydrate formed among the particles functions as a binder for the particles. Accordingly, the pellets thus obtained have an excellent strength. Therefore, it is possible to produce at low cost gas hydrate pellets which are excellent in storage efficiency because they have a high density and a high gas content, and also are excellent in storability with a low decomposition amount at depressurization and a low decomposition rate.

Moreover, using the apparatus according to the invention for producing gas hydrate pellets, in which the apparatus comprises a pair of compression rolls each having a plurality of molds in an outer peripheral surface thereof, the pair of compression rolls rotating respectively in opposite directions to each other, and feeding means for feeding the gas hydrate between the pair of compression rolls, or a first roll that rotate, a second roll and a third roll which are arranged close to and in parallel with the first roll, and each of which rotates in an opposite direction to that in which the first roll rotates, and feeding means for feeding a gas hydrate between the first roll and the third roll, wherein the second roll has a plurality of molds formed in an outer peripheral surface thereof, and the gas hydrate is dewatered by the first roll and the third roll, and subsequently the dewatered gas hydrate is compression-molded by the first roll and the second roll, gas hydrate pellets are produced by compression-molding a gas hydrate fed by the feeding means, in the molds formed in the outer peripheral surfaces of the pair of compression rolls rotating respectively in the opposite directions to each other. Accordingly, gas hydrate pellets can be produced by using the above-described process for producing gas hydrate. Therefore, gas hydrate pellets having an excellent storability can be produced at low cost.

DETAILED DESCRIPTION OF THE INVENTION

EXPLANATION OF REFERENCE NUMERALS

Figure 1:
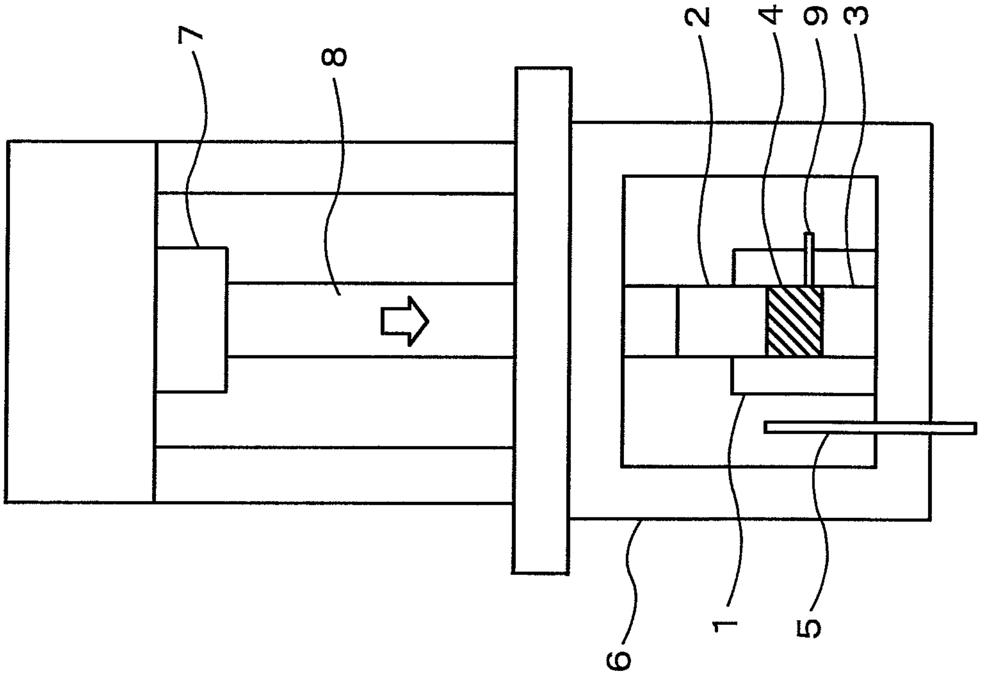
FIG. 1 illustrates a reciprocation-type pellet production apparatus.

| | |
|---|---|
| 1 | mortar |
| 2 | upper pestle |
| 3 | lower pestle |
| 4 | gas hydrate pellets |
| 5 | thermometer |
| 6 | pressure vessel |
| 7 | air cylinder |
| 8 | piston |
| 9 | drain outlet |
| 10 | pellet raw material |
| 11 | water |
| 12 | wedge water |
| 13 | surface-attached water |

-continued

| DETAILED DESCRIPTION OF THE INVENTION EXPLANATION OF REFERENCE NUMERALS | |
|---|---|
| 14 | in-particle water |
| 15 | void (gas) |
| 16 | gas hydrate |
| 17 | gap water |
| 18 | unsaturated part |
| 19 | saturated part |
| 20 | gas hydrate generated at molding |
| 21 | raw-material gas |
| 22 | raw-material water |
| 23 | gas hydrate |
| 24 | generator |
| 25 | pellet production apparatus |
| 26 | cooler |
| 27 | depressurizer |
| 28 | storage tank |
| 29 | pooled water |
| 30 | stirring propeller |
| 31 | pump |
| 32 | circulation line |
| 33 | heat exchanger |
| 34, 34a | pellet |
| 35 | dewatering line |
| 40 | compression roll |
| 41 | gas hydrate feeding means |
| 42, 42b | dewatering roll |
| 42a | compression dewatering roll |
| 43 | pocket |
| 45 | hopper |
| 46 | electric motor |
| 47 | screw feeder |
| 48 | dewatered gas hydrate |
| 50 | water-shield plate |
| 51 | end face (of compression roll) |
| 52 | drain pipe |
| 53 | pooled water |
| 54 | discharged water |
| 55 | front face of hopper |
| 56 | side face of hopper |
| 57 | slit |
| 58 | water flowing out in axial direction |
| 59 | drain gutter |
| 60 | outlet |
| 61 | drain gutter |
| 62 | outlet |
| 63 | water flowing out on side |
| 64 | drain gutter |
| 65 | outlet |
| 66 | blade |
| 67 | drain hole |
| 68 | hollow portion |
| 69 | discharged water |
| 70 | water-absorbent material |
| 71 | dewatering roller |
| 72 | discharged water |

Hereinafter, a process for producing gas hydrate pellets in which a gas hydrate generated from a raw-material gas and raw-material water is dewatered and simultaneously molded into pellets with compression-molding means under conditions suitable for generating the gas hydrate while the gas hydrate is generated from the raw-material gas and the raw-material water that exist among particles of the gas hydrate, and wherein a gas hydrate having a gas hydrate concentration of 40 to 70% by weight is dewatered and simultaneously compression-molded into pellets with compression-molding means under conditions suitable for generating the gas hydrate, will be described with reference to the drawings.

Here, the description will be given by taking as an example a case where a reciprocation-type pellet production apparatus illustrated in FIG. 1. Note that the same principle is applied also in a rotation-type production apparatus using compression rollers, which will be described later.

The reciprocation-type pellet production apparatus includes: a pressure vessel 6; an air cylinder 7 disposed on an upper portion of the pressure vessel 6; and a piston 8 penetrating to the inside of the pressure vessel. The pressure vessel 6 and the piston 8 are sealed by an O-ring. Inside the pressure vessel 6, an upper pestle 2 and a lower pestle 3 are disposed, and a mortar 1 is disposed around the pestles 2 and 3. In general, each of the upper pestle 2 and the lower pestle 3 has a columnar shape while the mortar 1 has a cylindrical shape. The piston 8, the upper pestle 2, the lower pestle 3, and the mortar 1 are concentrically arranged. Since the piston 8 and the upper pestle 2 are connected to each other, the upper pestle 2 inside the pressure vessel 6 can be pressurized by moving the piston 8 downward. There is a slight clearance of approximately 0.1 to 0.5 mm between the mortar 1 and each of the upper pestle 2 and the lower pestle 3, and each of the upper pestle 2 and the lower pestle 3 has such a structure as to be movable up and down.

Figure 2:
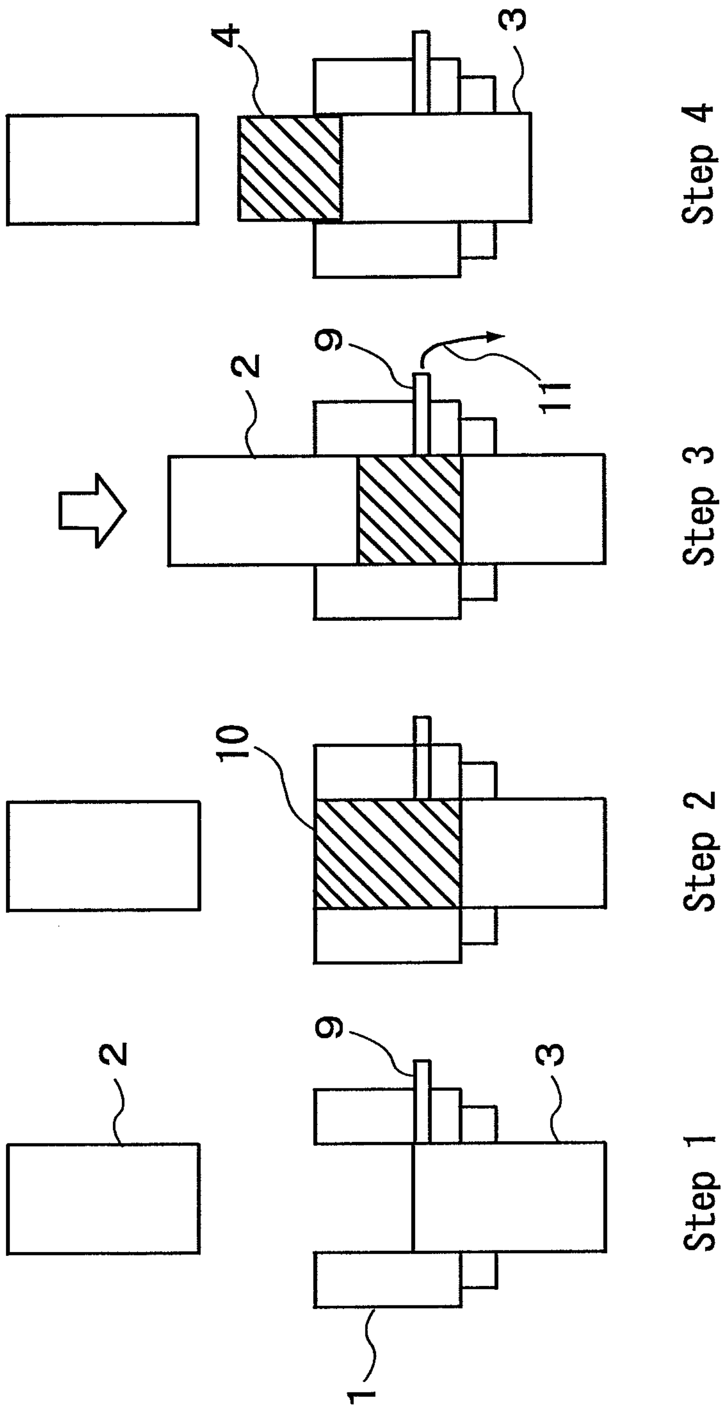
FIG. 2 is a mechanism diagram of pellet formation.

FIG. 2 illustrates a process of forming gas hydrate pellets through compression-molding.

First, the upper pestle 2 moves to the upper portion while the lower pestle 3 stays in the mortar 1 (Step 1). Next, a gas hydrate 10 is filled in the mortar 1 manually or automatically by using an unillustrated gas-hydrate filling device (Step 2). Then, the upper pestle 2 is pressed by the piston 8, and is thus moved downward to apply a molding load onto the gas hydrate 10 (Step 3). With this operation, the gas hydrate 10 is molded into a pellet 4. Finally, the upper pestle 2 is pulled upward by the piston 8, and the lower pestle 3 is moved upward by an unillustrated lower-pestle raising mechanism to bring the pellet 4 up above the upper portion of the mortar 1. Accordingly, the pellet 4 thus formed can be taken out of the mortar 1 (Step 4).

Figure 3:
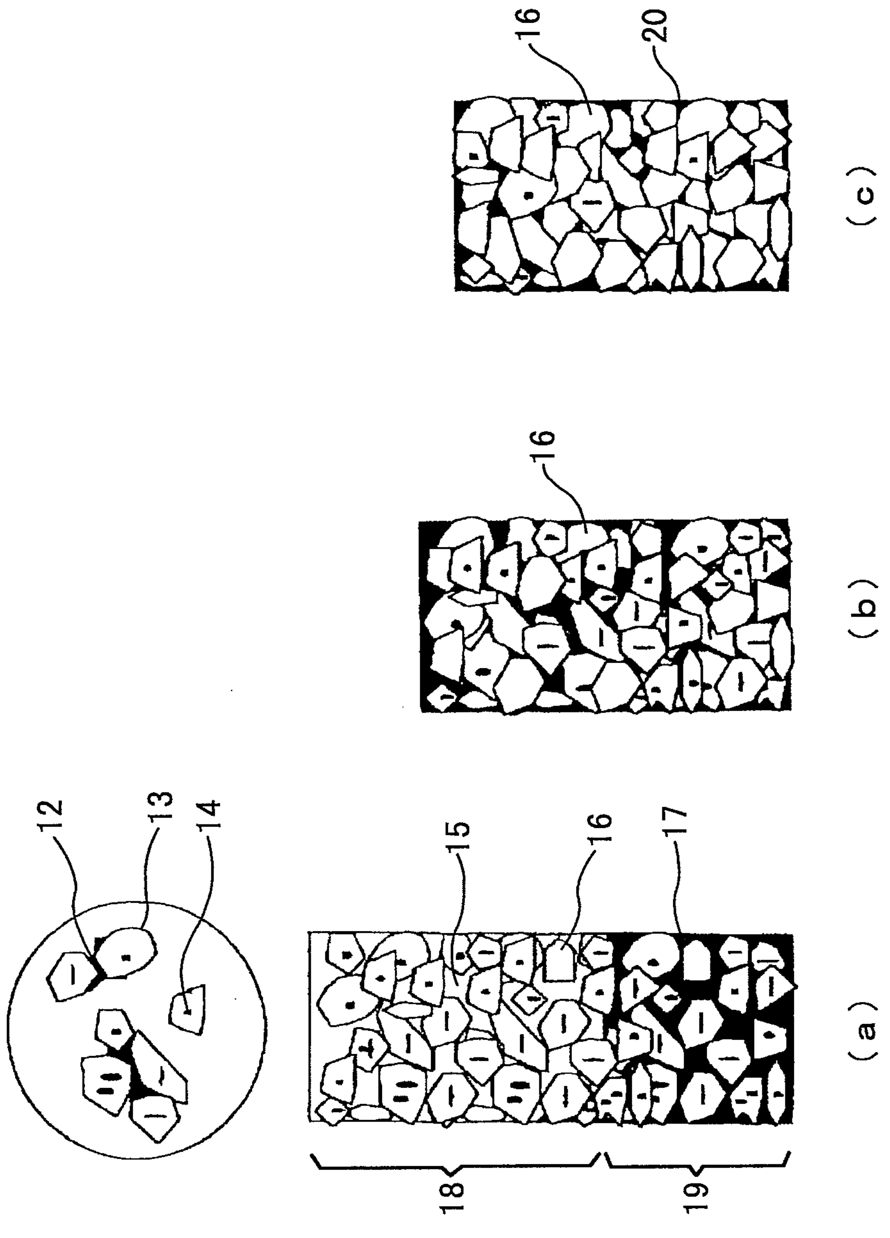
FIG. 3 is schematic views showing the states of gas hydrate in FIG. 2, Part (a) thereof shows a state in Step 2, Part (b) thereof shows a state in Step 3, and Part (c) thereof shows a state in a transition from Step 3 to Step 4.

In a part (generally, a lower part close to the bottom) of the gas hydrate 10 supplied to a molding portion illustrated in Step 2 of FIG. 2, the space among the gas hydrate particles is completely filled with water (gap water) 17, as illustrated in Part (a) of FIG. 3. In addition, in another part (generally, an upper part) of the gas hydrate 10, the space among the gas hydrate particles is not completely filled with water and thus forms avoid 15. In the void 15, the raw-material gas exists at the generating condition pressure. Moreover, so-called wedge water 12 exists between the gas hydrate particles. Further, the surfaces of the particles are not dry, and surface-attached water 13 exists thereon. The ratio of the void 15 (void ratio) in the pre-pressurization state is approximately 40 to 60% in general. In addition, in-particle water 14 exists in the inside of each gas hydrate particle. In Step 3 in FIG. 2, as illustrated in Part (b) of FIG. 3, the application of the molding load by the piston 8 compacts the gas hydrate particles, so that a surplus water 11 is discharged through a drain outlet 9. Although partially discharged to the outside as well, the gas existing in the void among the particles is trapped in the molding portion due to the compacting of the particles. The pressure of the gas becomes a high pressure that is equal to the molding load (at approximately 5 to 100 MPa) by the pressurization of the piston 8 in the molding. With such a high pressure, the equilibrium temperature of the gas hydrate becomes high. Accordingly, as illustrated in Part (c) of FIG. 3, the gap water 17 existing among the particles, the wedge water 12, and the in-particle water 14 that has exuded to the outside react with the high-pressurized gas to generate a gas hydrate 20.

In accordance with such action, the process for producing gas hydrate pellets in which a gas hydrate generated from a raw-material gas and raw-material water is dewatered and simultaneously molded into pellets with compression-molding means under conditions suitable for generating the gas hydrate while the gas hydrate is generated from the raw-material gas and the raw-material water that exist among particles of the gas hydrate, and wherein a gas hydrate having a gas hydrate concentration of 40 to 70% by weight is dewatered and simultaneously compression-molded into pellets with compression-molding means under conditions suitable for generating the gas hydrate, is capable of producing a high-density pellet with very little void in which the space among the raw material particles is almost filled with the gas hydrate. In addition, since the gas hydrate formed among the particles functions as a binder for the particles, the pellet thus obtained is rigid and has an excellent strength.

Figure 4:
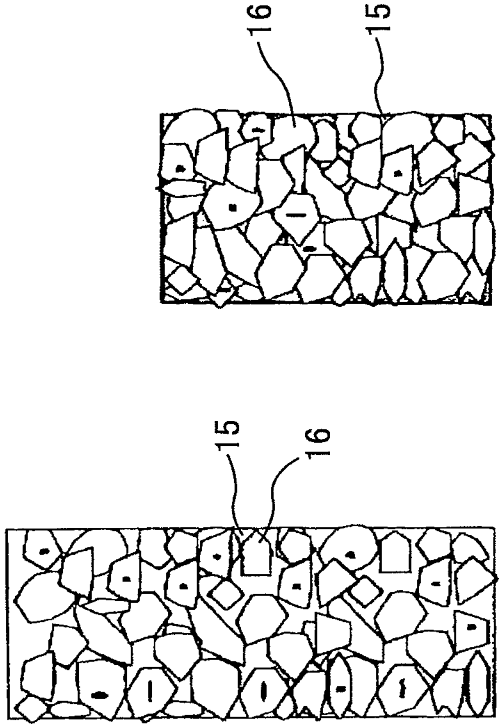
FIG. 4 shows Comparative Example which corresponds to FIG. 2 and has a raw-material gas hydrate ratio of 85%, Part (a) thereof corresponds to Step 2, and Part (b) thereof corresponds to Steps 3 to 4.

FIG. 4 shows Comparative Example. If the gas hydrate concentration is high, there exists the void 15 between a gas hydrate particle 16 and a particle 16 in Part (a) of FIG. 4 showing a state before molding. Even when the molding load is applied by the piston 8, the gas is discharged to the outside of the mold because the inter-particle void is dry. Accordingly, the gas pressure in the inside between the particles 16 becomes slightly higher than, or equal to, that in the outside of the mold. In addition, since the water content in the surfaces of the gas hydrate particles 16 is low, the generation of the gas hydrate 20 by the water in the surfaces and gas is unlikely to occur. As a result, a pellet thus molded has a large void ratio and a small density as shown in Part (b) of FIG. 4. In addition, the size of the particles constituting the pellet is small. As a result, the decomposition rate thereof is high.

Figure 5:
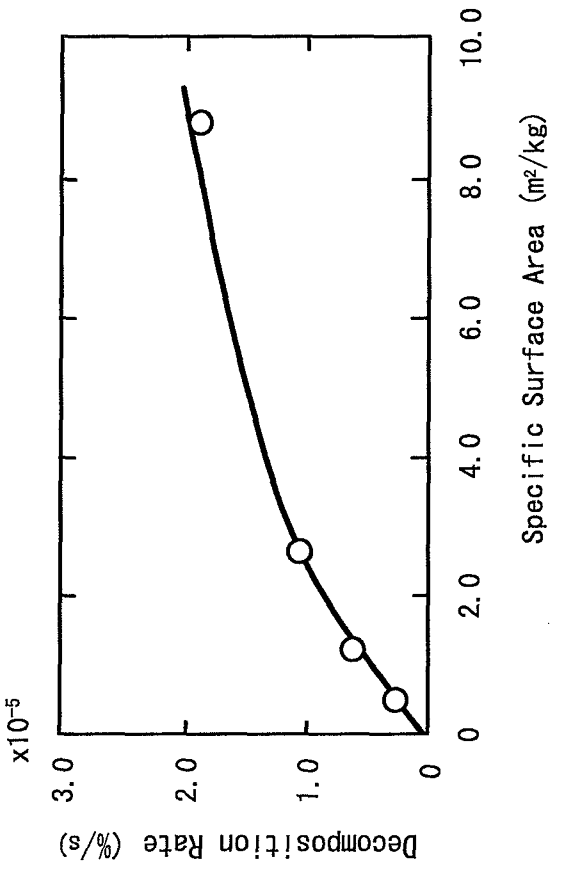
FIG. 5 is a graph showing a relation between a specific surface area and a decomposition rate.

FIG. 5 shows a relation between the specific surface area of the pellet and the decomposition rate thereof in storage (at −20° C.). A gas hydrate is decomposed from its surface. Accordingly, the smaller the specific surface area is, the slower the decomposition rate is. The specific surface area S is expressed by the following expression (1). The higher the pellet density is, or the larger the pellet-equivalent radius is, the smaller the specific surface area S is.

$$S=3/(\rho r) \quad (1)$$

where ρ is the pellet density and r is the pellet-equivalent radius.

Therefore, since the gas hydrate pellet according to the present invention has a high pellet density, the decomposition rate in storage can be reduced.

Figure 6:
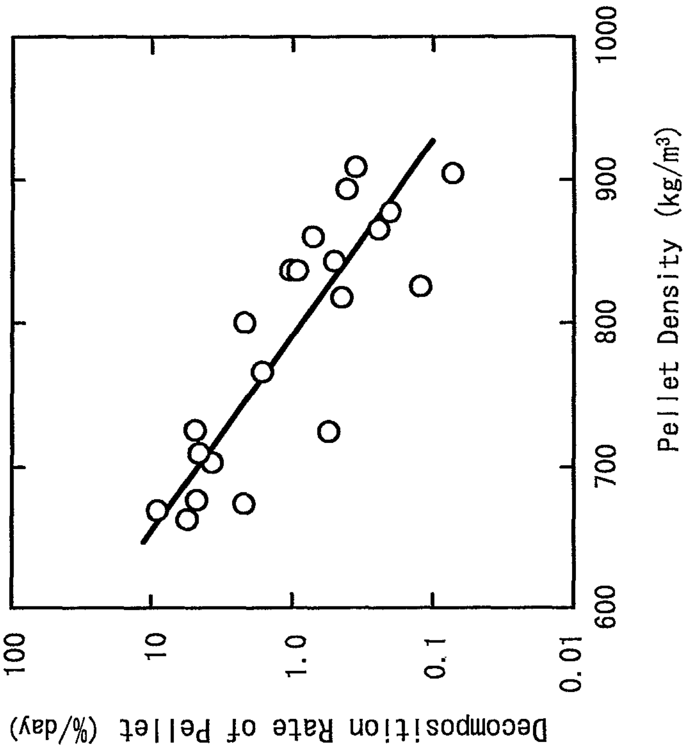
FIG. 6 is a graph showing a pellet density and the decomposition rate of a pellet.

FIG. 6 shows a relation between the pellet density and the decomposition rate of the pellet. Since the gas hydrate pellet according to the present invention has a high pellet density, the decomposition rate in storage can be reduced.

EXAMPLE 1

A gas hydrate was molded into a pellet by using the pellet production apparatus shown in FIG. 1 at 5 MPa and 2° C., that is, under the conditions suitable for generating the gas hydrate. The pellet had a columnar shape having a diameter of 13 mm and a height of 12 mm. The employed gas composition of the raw-material gas hydrate of the pellet was of the natural gas components (methane: 95%, propane: 5%). The molding pressure for the pellet ((the piston load (N)×(the cross-sectional area of the pellet ($m^2$)) was set at 1 to 100 MPa. The following result was obtained in a case where the gas hydrate concentration in the pellet raw material 10 is 50% by weight.

The volume of the raw material shown in Step 2 of FIG. 2 was 3.4 $cm^3$, out of which the volume of the gas hydrate was 1.2 $cm^3$ (a weight of 1.10 g), the volume of the water was 1.1 $cm^3$ (a weight of 1.10 g), and the volume of the void was 1.2 $cm^3$ (a gas weight of 0.04 g). Next, when the load was applied in the state shown in Step 3 of FIG. 2, the raw material was dewatered and 0.8 g of water was discharged through the drain outlet 9. The gas in the void 15 was compressed to have a volume of 1/2.8 by the piston, and the gas pressure inside the mold became 14 MPa. The equilibrium temperature of the gas hydrate 16 at this time was 16.5° C. Since its temperature at the start of the molding was 2° C., the supercooling degree for gas hydrate formation, which is obtained by subtracting (the reaction temperature) from (the equilibrium temperature), was 16.5° C.−2° C.=14.5° C. Even with a slight supercooling degree, a gas hydrate 20 is formed. Since there was a very large supercooling degree inside the mold, 0.34 g of gas hydrate was instantly formed from 0.3 g of remaining water and 0.04 g of remaining gas, resulting in the state in Step 4 of FIG. 2.

Since the gas hydrate 20 newly formed was formed tightly in the void among the raw material particles, the gas hydrate 20 newly formed brought about effects of reducing the void 15, increasing the density of the pellet, and reducing the specific surface area. In addition, the gas hydrate 20 also functioned as the binder for the particles, and accordingly, increased the mechanical strength of the pellet as well. Moreover, since the pressure in the formation was higher than ambient pressure, the hydration number of the gas hydrate 20 was high. As a result, the gas hydrate 20 having a high gas content was obtained. The density of the gas hydrate pellet was 900 kg/$m^3$, and the amount of decomposed gas hydrate due to depressurization from the generation pressure to the ambient pressure in the depressurizer after the cooling process was 1%. Accordingly, the natural gas hydrate pellet with a decomposition rate of 0.1%/day was obtained.

Figure 7:
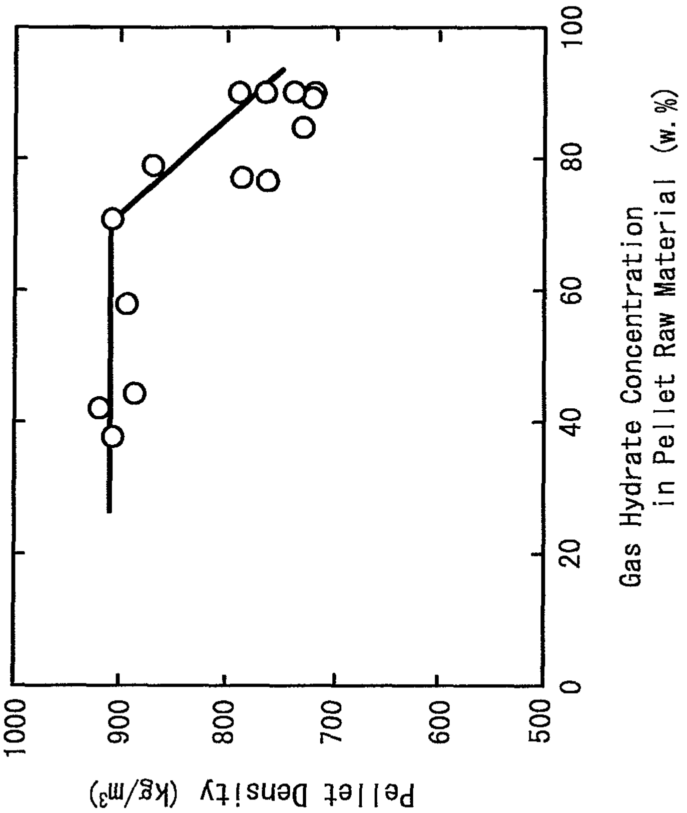
FIG. 7 is a graph showing a relation between a gas hydrate concentration in raw material and a bulk density of a pellet.

FIG. 7 shows a relation between the gas hydrate concentration in a pellet raw material and the density of the pellet. Here, the gas hydrate concentration in the pellet raw material refers to the weight ratio of the gas hydrate 16 in the pellet raw material 10, and the density of the pellet refers to a numerical value obtained by dividing the weight of the pellet 4 by the volume of the pellet 4 including the volume of the void. From this result, it is found that, when the gas hydrate concentration in the pellet raw material is in a range of approximately 20 to 80% by weight, the density has a value not less than 800 kg/$m^3$, which is considered as a bulk density making favorable the storability of the pellet 4.

Therefore, it is found that, from the viewpoint of bulk density, the concentration of the gas hydrate 16 to be supplied to the pellet production apparatus may be set at 20 to 80% by weight, and preferably 30 to 70% by weight which gives the highest value of approximately 900 kg/$m^3$.

Figure 8:
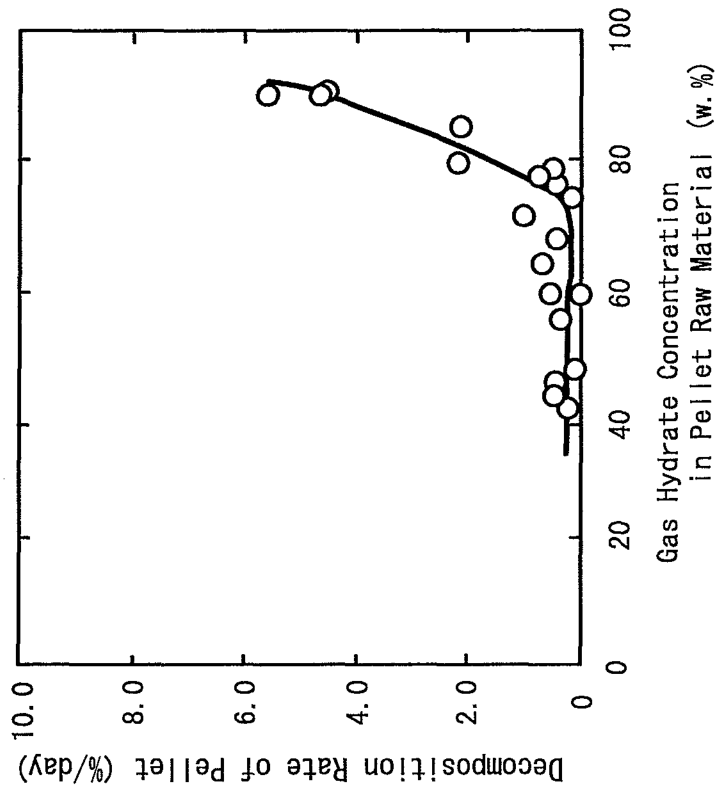
FIG. 8 is a graph showing a relation between the gas hydrate concentration in raw material and the decomposition rate of a pellet.

FIG. 8 shows a relation between the gas hydrate concentration in the pellet raw material and the decomposition rate of the pellet in storage at atmospheric pressure and −20° C. Here, the decomposition rate refers to the rate of change in concentration of the gas hydrate in the pellet 4 for a certain time period, and is a parameter that is indicative of a so-called self-preservation. From this result, it is found that, when the concentration of the gas hydrate 16 is in a range of approximately 40 to 80% by weight, the decomposition rate of the pellet 4 has the lowest value of approximately not more than 0.5% per day. Therefore, it is found that, from the viewpoint of decomposition rate, the concentration of the gas hydrate 16 to be supplied to the pellet production apparatus may be set at 40 to 80% by weight.

EXAMPLE 2

Figure 9:
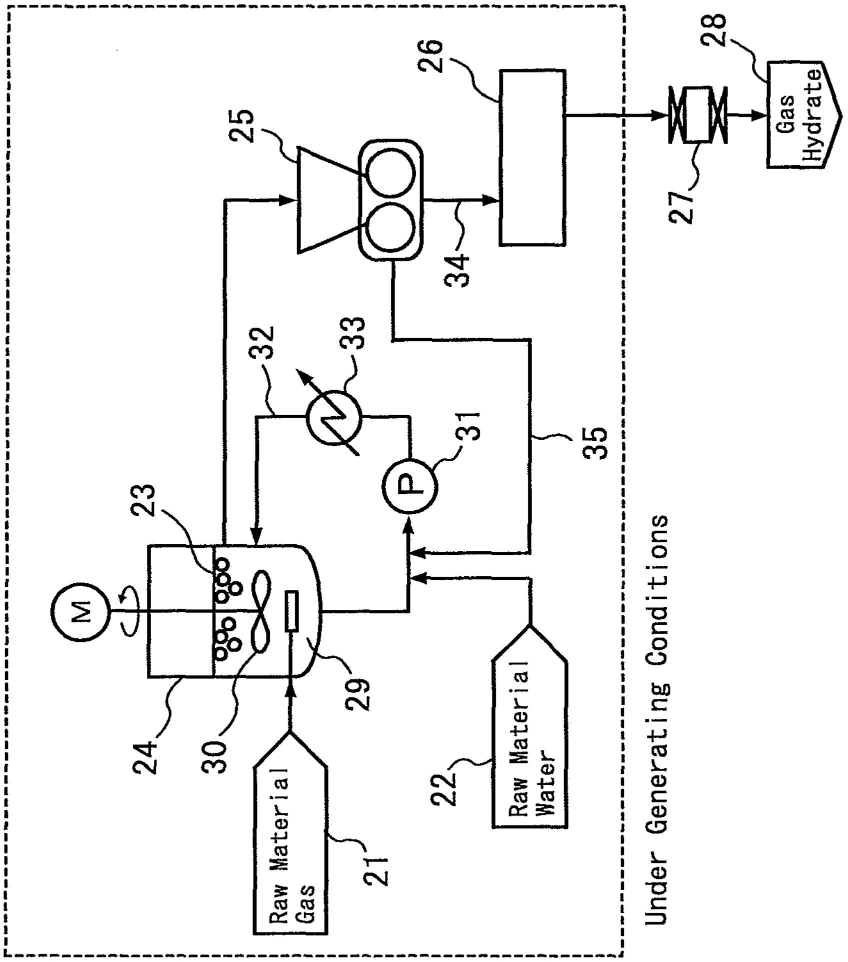
FIG. 9 is a production line according to Example 2 of a process for producing gas hydrate pellets of the present invention.

With a pellet production line illustrated in FIG. 9, the process for producing gas hydrate pellets according to the present invention was conducted. The pellet production line (hereinafter, called a "production line") is formed of: a generator 24 for a gas hydrate 23; a gas hydrate pellet-production apparatus 25 (hereinafter, called a "production apparatus"), which is compression-molding means for producing pellets from the gas hydrate 23 thus generated; a cooler 26 for cooling the pellets thus produced; a depressurizer 27 for depressurizing the pellet thus cooled below atmospheric pressure; and a storage tank 28 for storing the pellets thus depressurized.

The generator 24 generates the gas hydrate 23 from a raw-material gas 21 and raw-material water 22. Specifically, the generator 24 generates the gas hydrate 23 by a method (a gas-liquid stirring method) in which stirring is performed with a stirring propeller 30 while the raw-material gas 21 is blown into a pooled water 29 under high pressure/low temperature generating conditions (for example, at 5.4 MPa and 4° C.) (for example, refer to Japanese patent application Kokai publication No. 2000-302701). Part of the pooled water 29 is sent to a circulation line 32 by a pump 31, and is returned to the generator 24 after reaction heat thereof is removed by a heat exchanger 33. In addition, the pooled water 29 consumed for the generation of the gas hydrate 23 is replenished with the raw-material water 22 from the circulation line 32.

Figure 10:
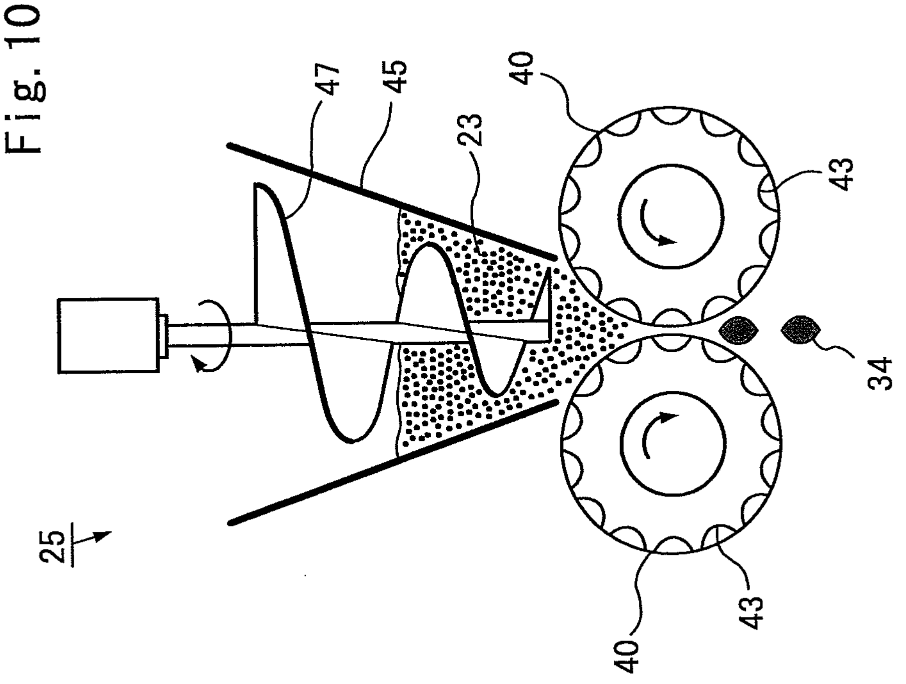
FIG. 10 is a cross-sectional view of a briquetting-roll-type apparatus for producing gas hydrate pellets.

The pellet production apparatus 25 may be of any of a compression roll type, a briquetting roll type, and a tabletting type, and is desirably of the briquetting roll type in view of the production efficiency. For this reason, a so-called briquetting machine, as shown in FIG. 10, is used in this example. The gas hydrate 23 generated by the generator 24 is fed between a pair of compression rolls 40, which are made of a metal, by feeding means formed of a hopper 45 and a screw feeder 47. The gas hydrate 23 is thus taken in by pockets 43, which are molds, and thereby is compression-molded while being dewatered, so that pellets 34 are produced. In this way, the dewatering of the gas hydrate 23 as well as the generation and the compression-molding of the gas hydrate 20 are simultaneously performed in the pellet production apparatus 25. Accordingly, the production line can be simplified. It should be noted that water generated through the dewatering in the compression-molding is returned to the generator 24 through a dewatering line 35 so as to be reused.

The cooler 26 cools the pellets 34 thus produced to a stable temperature of 0° C. or less, for example −20° C.

The above-described processes are conducted at high pressure and low temperature, that is, under the conditions suitable for generating the gas hydrate. For this reason, the depressurizer 27 is provided to depressurize the pellets after the cooling so that the pellets should be able to be stored in the storage tank 28 at atmospheric pressure.

In the above-described production line, the pellets 34 were produced from gas hydrate 3 generated under conditions shown in Table 1, where the compositions of the raw-material gas 21 were determined in consideration of an ideal case (Case 1) and cases simulating an actual plant (Cases 2 and 3).

In addition, the supercooling degree refers to a difference between a generation temperature and a theoretical equilibrium temperature of the gas hydrate, and is a parameter determining how the gas hydrate is generated.

Note that the pressure for compression-molding in the production of the pellets 34 was set at 2 to 3 ton/cm in the axial direction of the rolls 40.

TABLE 1

| Case | Composition of Raw Material Gas | Generation Pressure (MPa) | Generation Temp. (° C.) | Supercooling Degree (° C.) | Gas Hydrate Concentration (%) | Pellet Density (kg/m$^3$) |
|---|---|---|---|---|---|---|
| 1 | Methane: 100% | 5.4 | 3 | 4.7 | 40 | 900 |
| 2 | Methane: 90% Ethane: 5% Propane: 4% Butane: 1% | 4.4 | 3 | 3.5 | 60 | 900 |
| 3 (Comparative Example) | Same As Above | 4.4 | 3 | 3.5 | 90 | 720 |

A gas hydrate of Case 1 was fed to the pellet production apparatus at a raw-material gas hydrate concentration of 40%, and thereby a spherical pellet having a diameter of 20 mm was molded. As a result, the decomposition amount in the depressurizer was 1%, and a methane hydrate pellet having a pellet density of 900 kg/m$^3$ and a decomposition rate of 0.2%/day was obtained.

A gas hydrate of Case 2 was fed to the pellet production apparatus at a raw-material gas hydrate concentration of 60% by weight, and thereby an almond-form pellet having a diameter of 20 mm was molded. As a result, the decomposition amount in the depressurizer was 1%, and a natural gas hydrate pellet having a pellet density of 900 kg/m$^3$ and a decomposition rate of 0.1%/day was obtained.

The setting of the gas hydrate concentration in the pellet raw material at 20 to 80% by weight caused, during the pellet molding, dewatering and gas hydrate generating reaction of a gas existing in the void with water (wedge water, surface water, in-particle water, gap water (which has not been removed)) remaining on the surface of the pellet and in the inside thereof. As a result, the pellet having a density of 900 kg/m$^3$ was formed. The pellet had a decomposition rate of 0.2%/day when stored at −20°.

The result of the above-described study shows that the concentration of the gas hydrate 23 to be supplied to the pellet production apparatus 25 may be set at 20 to 80% by weight, and preferably 40 to 70% by weight, in order to produce the pellet 34 having an excellent storability with a high bulk density and a low decomposition rate.

Next, apparatus for producing gas hydrate pellets in which the apparatus includes a pair of compression rolls each having a plurality of molds in an outer peripheral surface thereof (hereinafter, referred to as "apparatus for producing gas hydrate pellets according to the present invention") will be described with reference to the drawings.

Figure 11:
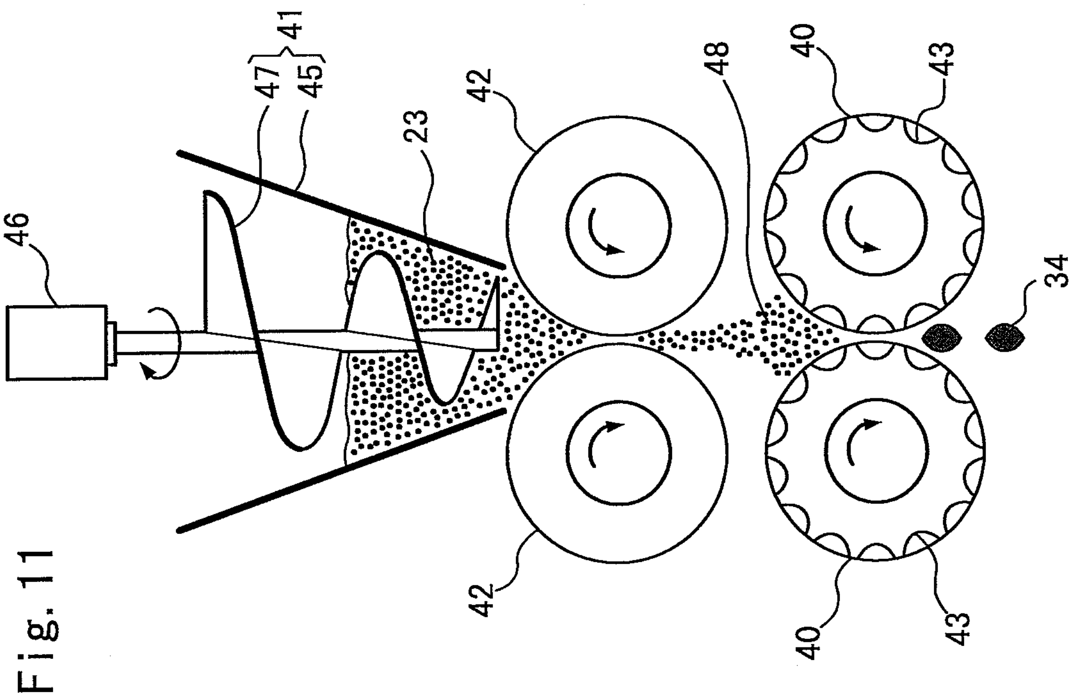
FIG. 11 is a cross-sectional view of an apparatus for producing gas hydrate pellets according to a first embodiment of the present invention.

FIG. 11 illustrates an apparatus for producing gas hydrate pellets according to a first embodiment of the invention according to the present invention.

The apparatus for producing gas hydrate pellets is characterized in that a pair of dewatering rolls 42, which are dewatering means, are arranged between a pair of compression rolls 40 and gas hydrate feeding means 41 in a conventional briquetting machine as illustrated in FIG. 10. The pair of compression rolls 40 are arranged close to each other and in parallel with each other in their axial directions. A plurality of pockets 43, each of which is a pellet mold, are formed in the outer peripheral surface of each compression roll 40. The pair of dewatering rolls 42 are arranged directly above the pair of compression rolls 40 in such a manner as to be parallel therewith. Although the outer peripheral surface of each dewatering roll 42 is smooth, a plurality of dewatering grooves may be formed in at least one of a circumferential direction and an axial direction thereof in order to improve the drainage efficiency in the dewatering. In addition, it is preferable that each dewatering roll 42 have the same outer diameter as that of each compression roll 40. Each pair of the pair of compression rolls 40 and the pair of dewatering rolls 42 are configured to rotate respectively in the opposite directions to each other by unillustrated driving means.

The gas hydrate feeding means 41 continuously feeds the gas hydrate 23 between the dewatering rolls 42 and is formed of a hopper 45 and a screw feeder 47 that is rotationally driven by an electric motor 46.

The operation of the apparatus for producing gas hydrate pellets having the above-described structure will be described below.

The gas hydrate 23 fed onto the pair of dewatering rolls 42 by the gas hydrate feeding means 41 is caught between the rotating dewatering rolls 42 to be pressurized, and thereby dewatered. A gas hydrate 48 after the dewatering falls down on the compression rolls 40 located immediately below, and is compression-molded into pellets 34 in the pockets 43 of the pair of compression rolls 40. At this time, water exudes from the gas hydrate 48 due to the compression-molding. However, since the gas hydrate 48 has been sufficiently dewatered in advance by the dewatering rolls 42, no large amount of water is pooled on the compression rolls 40.

Using the apparatus for producing gas hydrate pellets as described above makes it possible to produce gas hydrate pellets by using the aforementioned process for producing gas hydrate pellets. In addition, since no large amount of water is pooled on the pair of compression rolls, the feeding of the gas hydrate is not interfered. Accordingly, the production efficiency of gas hydrate pellets can be prevented from being deteriorated.

Figure 12:
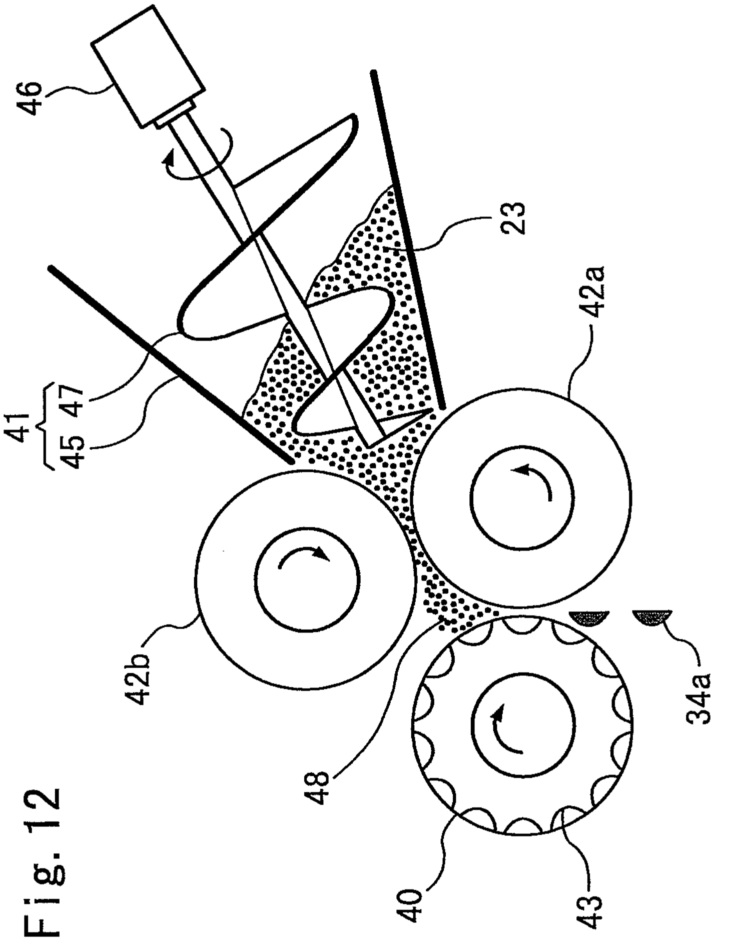
FIG. 12 is a cross-sectional view of a modification of the apparatus for producing gas hydrate pellets according to the first embodiment of the present invention.

FIG. 12 illustrates a modification of the apparatus for producing gas hydrate pellets according to the first embodiment.

This modification includes a dewatering roll 42*a*, which is a first roll; a compression roll 40, which is a second roll and is arranged close to, and in parallel with, the compression dewatering roll 42*a* in a substantially horizontal direction; and a dewatering roll 42*b*, which is a third roll and is arranged also close to, and in parallel with, but obliquely above, the compression dewatering roll 42*a*. Although the outer peripheral surface of each of the compression dewatering roll 42*a* and the dewatering roll 42*b* is smooth, dewatering grooves may be formed in at least one of a circumferential direction and an axial direction thereof in order to improve the drainage efficiency in the dewatering. In addition, a plurality of pockets 43 are formed in the outer peripheral surface of the compression roll 40. Note that, it is desirable that the outer diameters of these three rolls are equal to one another. A gas hydrate supply means 46 has the same structure as that in the first embodiment, but is inclined so as to be able to feed the gas hydrate 23 between the compression dewatering roll 42*a* and the dewatering roll 42*b*.

In this modification, after being dewatered between the compression dewatering roll 42*a* and the dewatering roll 42*b*, the gas hydrate 23 is fed between the compression dewatering roll 42*a* and the compression roll 40, and is compression-molded into semi-spherical pellets 34*a* in the pockets 43. This structure makes it possible to reduce the number of rolls, and accordingly, to reduce the equipment cost.

Figure 13:
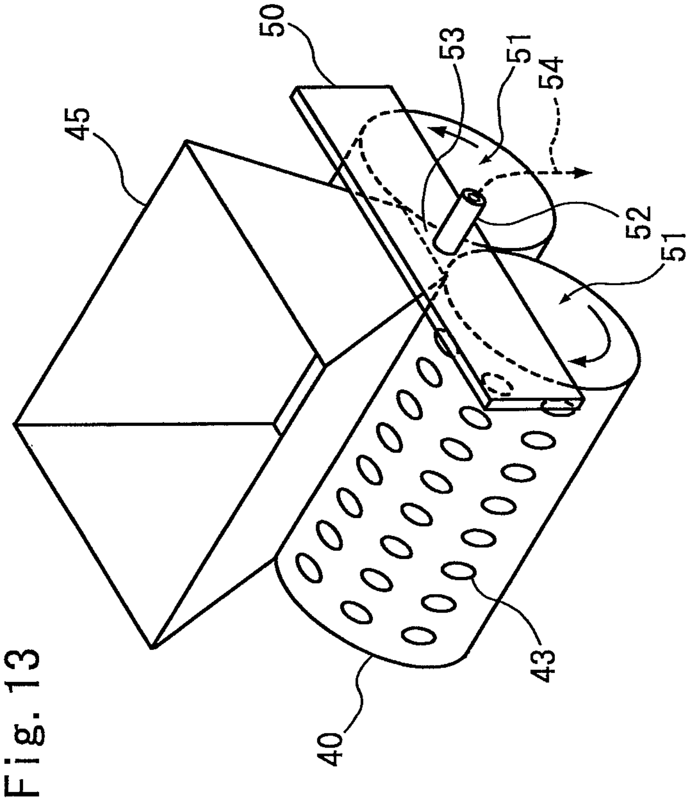
FIG. 13 is a perspective view of an apparatus for producing gas hydrate pellets according to a second embodiment of the present invention.

FIG. 13 illustrates an apparatus for producing gas hydrate pellets according to a second embodiment of the present invention.

In this embodiment, a water-shield plate 50 and a drain pipe 52, which are drain means, are installed in an apparatus for producing gas hydrate pellets including: a pair of compression rolls 40 each having pockets 43 formed in the outer peripheral surface thereof; and gas hydrate supply means. The water-shield plate 50 is formed of a flat plate covering at least the upper half of end faces 51 of the compression rolls 40. The drain pipe 52 is disposed to penetrate the water-shield plate 50 and leads to a space above the compression rolls 40.

With this structure, pooled water 53 flows on the water-shield plate 50 into the drain pipe 52 so as to be discharged as discharged water 54, while being generated on the compression rolls 40 by compression-molding, in the pockets 43, the gas hydrate 23 fed from the hopper 45 onto the compression rolls 40. Accordingly, the production efficiency of gas hydrate pellets can be improved.

Note that, it is desirable that the compression rolls 40 be slightly inclined toward the water-shield plate 50 in order to improve the drain efficiency. Moreover, the water-shield plate 50 may be provided on both sides of the compression rolls 40 instead of only one side of the compression rolls 40.

Figure 14:
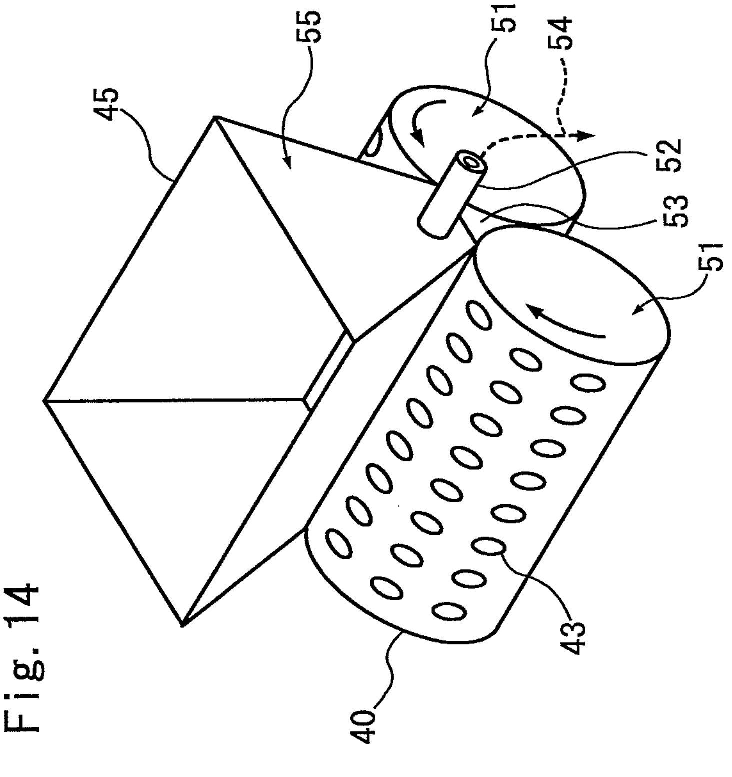
FIG. 14 is a perspective view of an apparatus for producing gas hydrate pellets according to a third embodiment of the present invention.

FIG. 14 illustrates an apparatus for producing gas hydrate pellets according to a third embodiment of the present invention.

In this embodiment, a drain pipe 52 is provided as the drain means directly in a front face 55 of the hopper 45. If pooled water 53 on the compression rolls 40 reaches the inside of the hopper 45, the pooled water 53 is discharged through the drain pipe 52.

Figure 15:
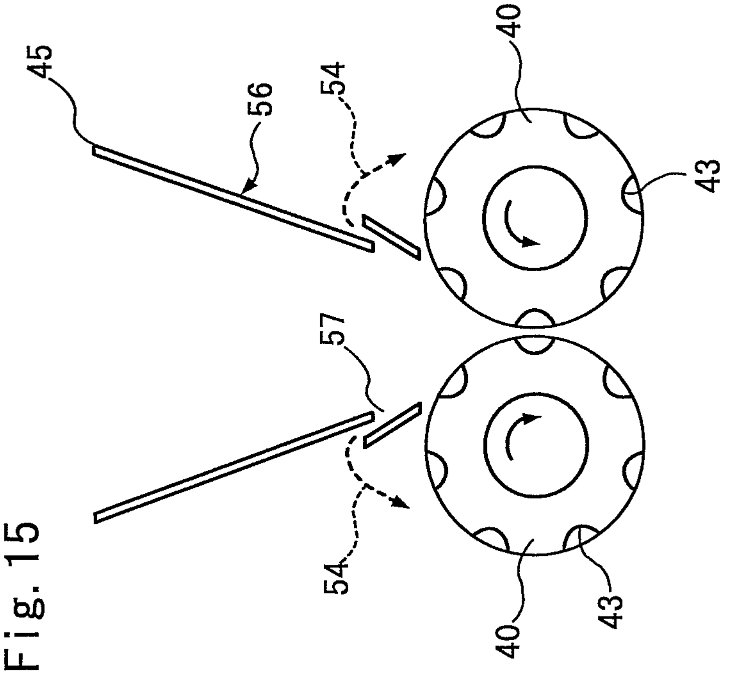
FIG. 15 is a cross-sectional view of an apparatus for producing gas hydrate pellets according to a fourth embodiment of the present invention.

FIG. 15 illustrates an apparatus for producing gas hydrate pellets according to a fourth embodiment of the present invention.

In this embodiment, slits 57 are formed in side faces 56 of the hopper 45 as the drain means. As in the case of the third embodiment, if pooled water 53 on the compression rolls 40 reaches the inside of the hopper 45, the pooled water 53 is discharged through the slits 57. Note that, a labyrinth may be provided instead of the slit 57 in order to keep the gas hydrate in the hopper 45 from flowing out together with discharged water.

Figure 16:
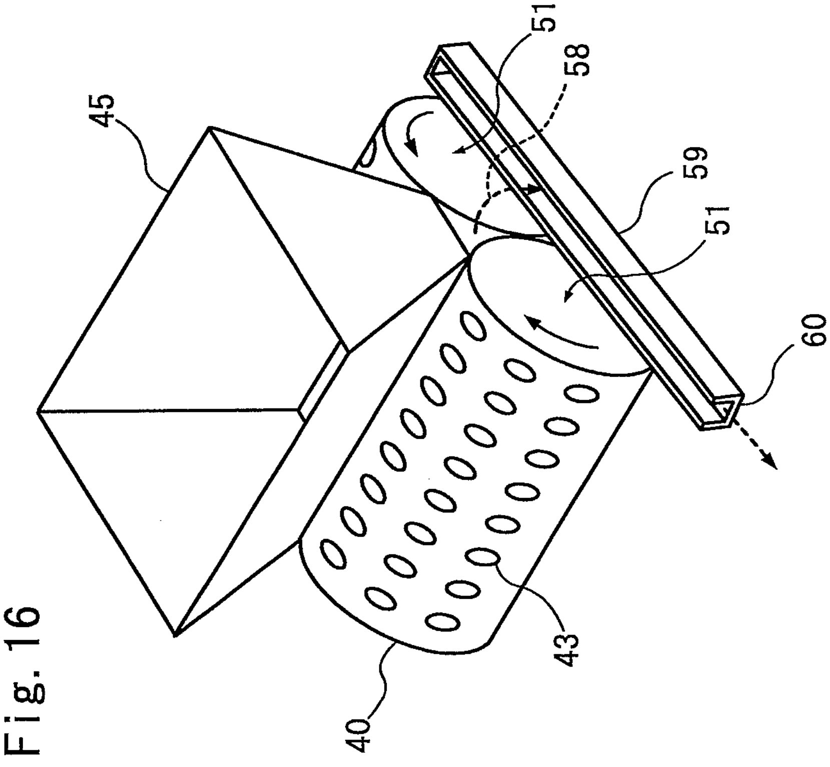
FIG. 16 is a perspective view of an apparatus for producing gas hydrate pellets according to a fifth embodiment of the present invention.

FIG. 16 illustrates an apparatus for producing gas hydrate pellets according to a fifth embodiment of the present invention.

In this embodiment, a drain gutter 59 is disposed to extend in a direction perpendicular to the axial directions of the compression rolls 40, as the drain means. The drain gutter 59 is located close to end faces 51 of the compression rolls 40, and is inclined in such a manner that an outlet 60 thereof is located at a lower position so as to smooth the water flow. With this structure, water 58 that has flown out in the axial direction of the compression rolls 40 is discharged through the drain gutter 59. Note that, it is desirable that the compression rolls 40 be slightly inclined toward the drain gutter 59 in order to improve the drain efficiency. Moreover, the drain gutter 59 may be provided on both sides of the compression rolls 40 instead of only one side of the compression rolls 40.

Figure 17:
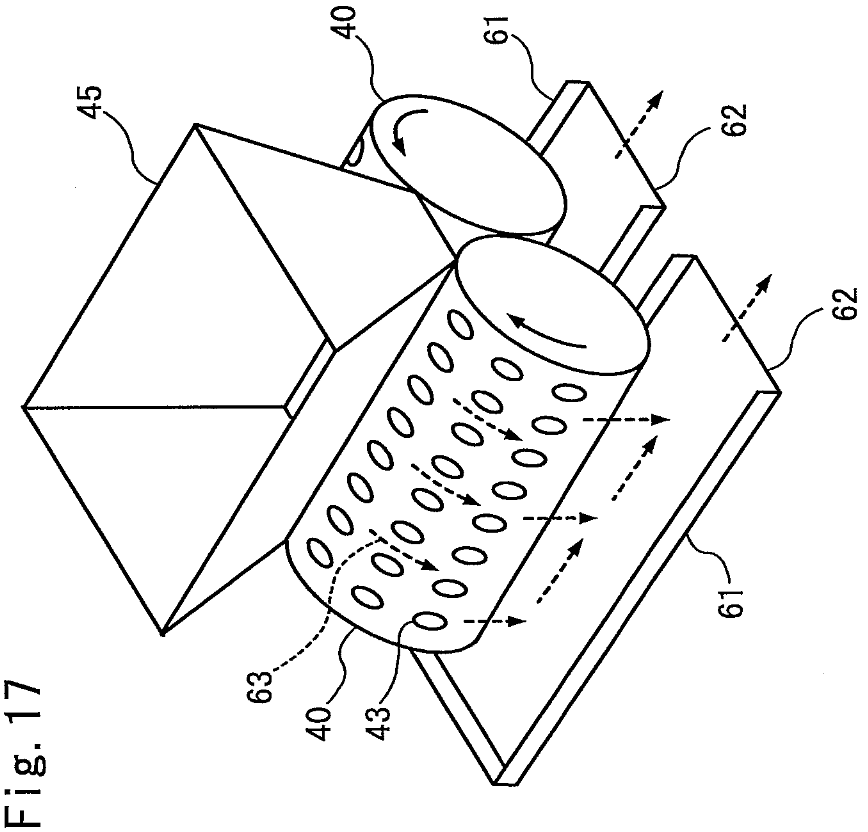
FIG. 17 is a perspective view of an apparatus for producing gas hydrate pellets according to a sixth embodiment of the present invention.

FIG. 17 illustrates a gas hydrate pellets production apparatus according to a sixth embodiment of the present invention.

In this embodiment, drain gutters 61 are disposed as the drain means respectively below the compression rolls 40. The drain gutters 61 are longer than the compression rolls 40, and are arranged at positions slightly separated downward from the compression rolls 40. In addition, the drain gutters 61 are slightly inclined in such a manner that outlets 62 thereof are located at lower positions so as to smooth the water flow in the drain gutters 61. With this structure, water 63 that has flown out on the outer peripheral surfaces of the compression rolls 40 is discharged through the drain gutters 61.

Figure 18:
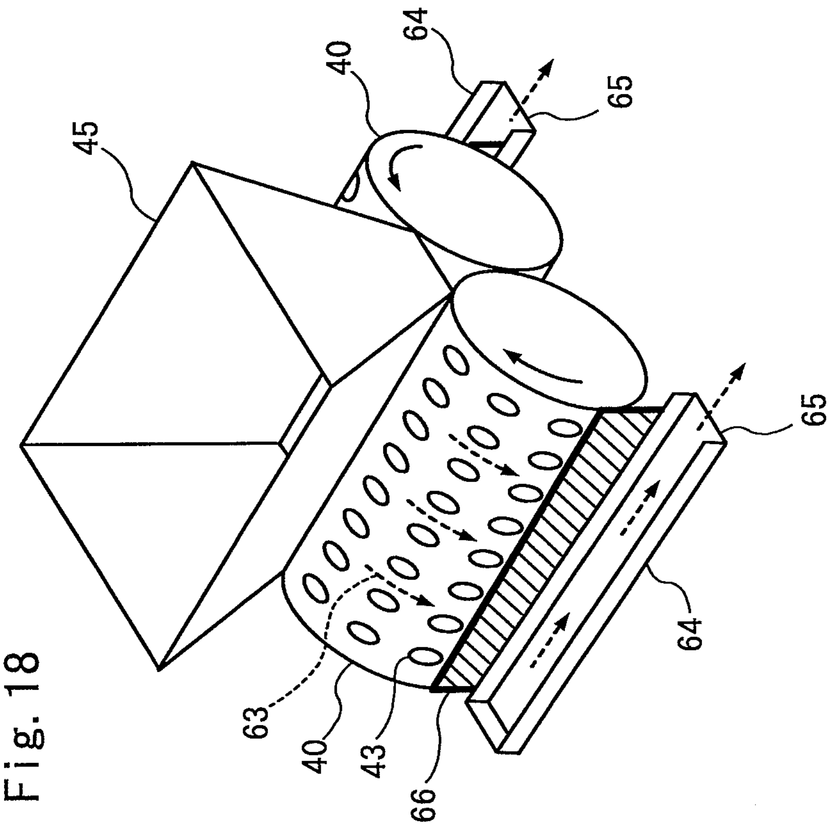
FIG. 18 is a perspective view of an apparatus for producing gas hydrate pellets according to a seventh embodiment of the present invention.

FIG. 18 illustrates an apparatus for producing gas hydrate pellets according to a seventh embodiment of the present invention.

In this embodiment, drain gutters 64 are disposed as the drain means respectively at the sides of the compression rolls 40. The drain gutters 64 are longer than the compression rolls 40, and are arranged near the respective side portions of the compression rolls 40. In addition, the drain gutters 64 are slightly inclined in such a manner that outlets 65 thereof are located at lower positions so as to smooth the water flow in the drain gutters 64. A plate-shaped blade 66 made of an elastic material such as rubber stands upright along a side face of each drain gutter 64 on the corresponding compression roll 40 side in such a manner that an upper end portion of the blade 66 is in contact with the outer peripheral portion of the corresponding compression roll 40. With this structure, water 63 that has flown out on the outer peripheral surfaces of the compression rolls 40 is guided by the blades 66 into the drain gutters 64 so as to be discharged.

Figure 19:
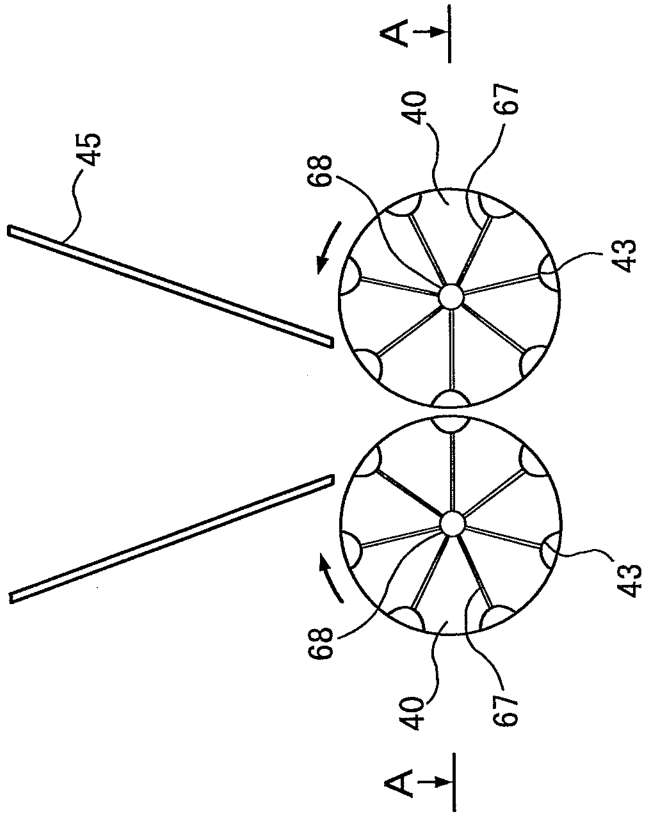
FIG. 19 is a perspective view of an apparatus for producing gas hydrate pellets according to an eighth embodiment of the present invention.
Figure 20:
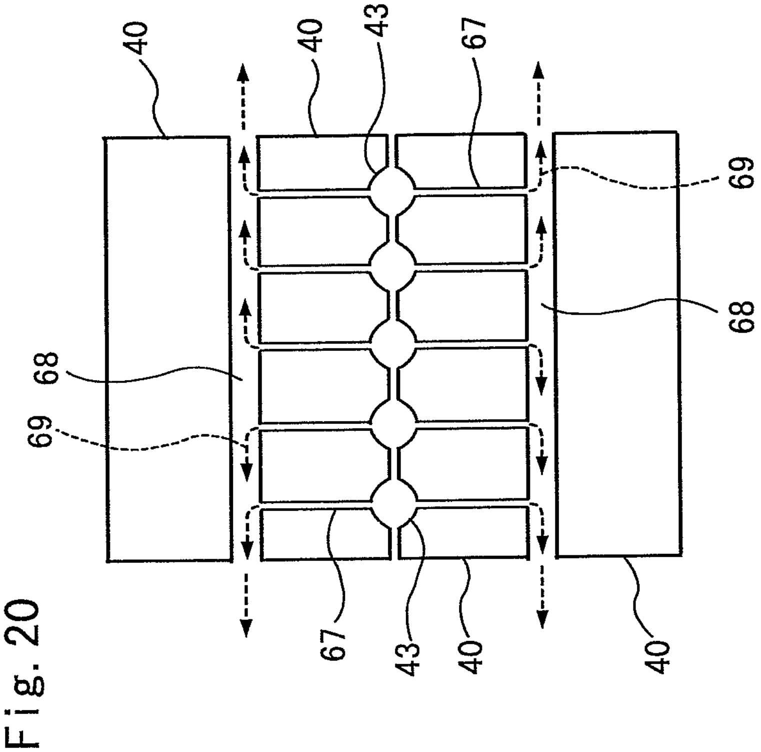
FIG. 20 is a cross-sectional view in the direction of the arrows A-A shown in FIG. 19.

FIG. 19 and FIG. 20 illustrate an apparatus for producing gas hydrate pellets according to an eighth embodiment of the present invention.

In this embodiment, drain holes 67 communicating with the outside of the compression rolls 40 are provided as the drain means in pockets 43. A hollow portion 68 having an opening end on at least one of the end faces is formed in the inside of each compression roll 40. Each of the pockets 43 communicates with the corresponding hollow portion 68 through the corresponding drain hole 67 extending from the bottom portion of the pocket 43. With this structure, water 69 generated by compression molding in each pocket 43 in each compression roll 40 flows to the hollow portion 68 through the drain hole 67 from the bottom portion of the pocket 43, and is then discharged to the outside of the compression roll 40 from the end face with the opening end.

Note that, it is desirable that, if the opening end is provided in only one end face of each hollow portion 68, the compression rolls 40 be slightly inclined toward the one end face in order to improve the drain efficiency. Moreover, sucking the inside of each hollow portion 68 with a pump or the like makes it possible to further improve the drain efficiency.

Note that, it is desirable that the inner diameter of each drain hole 67 be 0.5 to 5.0 mm, or that a water-permeable material, such as a mesh made of a metal or a sintered metal, for example, be disposed on the inner surface of each pocket 43, in order to prevent the drain holes 67 from being clogged by the gas hydrate flowing from the pockets 43 thereinto along with the water 69.

Figure 21:
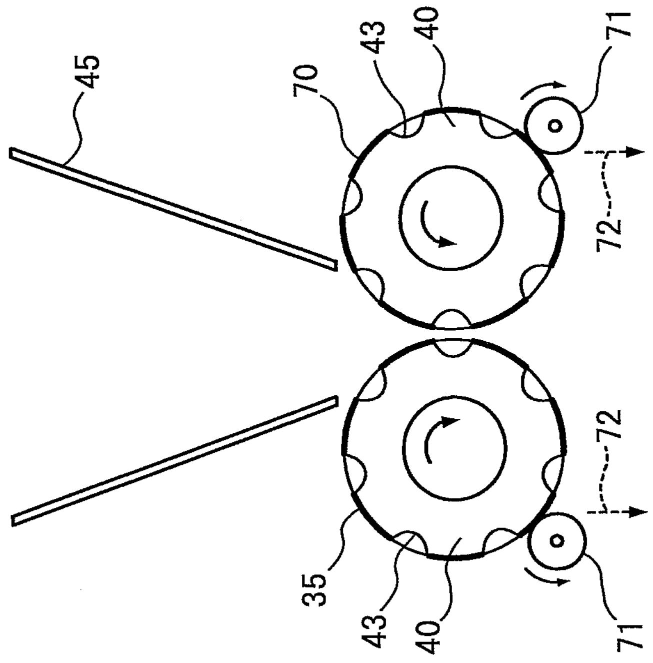
FIG. 21 is a cross-sectional view of an apparatus for producing gas hydrate pellets according to a ninth embodiment of the present invention.

FIG. 21 illustrates an apparatus for producing gas hydrate pellets according to a ninth embodiment of the present invention.

In this embodiment, a water-absorbent material 70 is attached as the drain means on the outer peripheral surface of each compression roll 40, and a dewatering roller 71 that presses the water-absorbent material 70 on each outer peripheral surface is provided. The water-absorbent material 70 is attached with a substantially constant thickness on a flat surface, that is, portions except the pockets 43, in the outer peripheral surface of each compression roll 40. As the material for the water-absorbent material 70, a sponge or a water-absorbent resin may be used, for example. Each dewatering roller 71 is disposed on a lower portion of the compression roll 40 in such a manner as to, while rotating, press the outer peripheral surface with unillustrated pressing means, for example, a hydraulic cylinder. With this structure, water generated by compression-molding of the gas hydrate is absorbed by the water-absorbent materials 70 on the outer peripheral surfaces of the compression rolls 40. The water thus absorbed is squeezed out by the pressure of the dewatering rollers 71, thereby being discharged downward as discharged water 72.

Note that, when a material also having elasticity, such as a rubber sponge, is used as the water-absorbent materials 70, the water-absorbent materials 70 fill up the gap between the compression rolls 40, so that burrs which would be otherwise attached to pellets 7 can be eliminated.

Any of all the above-described embodiments of apparatus for producing gas hydrate pellets may be implemented in combination as appropriate.

Moreover, the production cost of gas hydrate pellets can be further reduced by returning discharged water to a gas hydrate generating process for reuse.

We claim:

1. A process for producing gas hydrate pellets, in which a gas hydrate generated from a raw-material gas and raw-material water is dewatered and simultaneously molded into pellets with compression-molding means under conditions suitable for generating the gas hydrate while the gas hydrate is generated from the raw-material gas and the raw-material water that exist among particles of the gas hydrate.

2. The process for producing gas hydrate pellets, according to claim 1, wherein the compression-molding means is briquetting rolls including a pair of rolls each having a plurality of pellet molds in an outer peripheral surface thereof, the pair of rolls rotating respectively in opposite directions to each other.

3. The process for producing gas hydrate pellets, according to claim 1, wherein the gas hydrate is made from a natural gas, and the generating conditions are a pressure of 1 to 10 MPa and a temperature of 0 to 10° C.

4. A process for producing gas hydrate pellets, wherein a gas hydrate having a gas hydrate concentration of 40 to 70% by weight is dewatered and simultaneously compression-molded into pellets with compression-molding means under conditions suitable for generating the gas hydrate.

5. The process for producing gas hydrate pellets, according to claim 4, wherein the compression-molding means is briquetting rolls including a pair of rolls each having a plurality of pellet molds in an outer peripheral surface thereof, the pair of rolls rotating respectively in opposite directions to each other.

6. The process for producing gas hydrate pellets, according to claim 4, wherein the gas hydrate is made from a natural gas, and the generating conditions are a pressure of 1 to 10 MPa and a temperature of 0 to 10° C.

* * * * *